United States Patent [19]

Thunberg et al.

[11] 3,947,496

[45] Mar. 30, 1976

[54] PROCESS FOR RECOVERING GLYCINE FROM SODIUM SULFATE SOLUTIONS

[75] Inventors: Jon Carl Thunberg, Amherst, N.H.; Robert Wright Bragdon, Marblehead, Mass.; William Philip Moore, Hudson, N.H.

[73] Assignee: W. R. Grace & Co., New York, N.Y.

[22] Filed: Apr. 29, 1975

[21] Appl. No.: 572,841

Related U.S. Application Data

[63] Continuation-in-part of Ser. No. 517,469, Oct. 24, 1974, which is a continuation-in-part of Ser. No. 442,543, Feb. 14, 1974, abandoned, which is a continuation-in-part of Ser. No. 319,539, Dec. 29, 1972, Pat. No. 3,808,269.

[52] U.S. Cl............................................. 260/534 R
[51] Int. Cl.².......................................... C07C 99/12
[58] Field of Search ..................... 260/534 R, 534 C

[56] References Cited
UNITED STATES PATENTS

| | | | |
|---|---|---|---|
| 3,433,832 | 3/1969 | Swanson et al.................. | 260/534 S |
| 3,875,221 | 4/1975 | Mihara et al..................... | 260/534 R |

*Primary Examiner*—Vivian Garner
*Attorney, Agent, or Firm*—Elton Fisher

[57] ABSTRACT

Glycine can be recovered from an aqueous starting solution of glycine and sodium sulfate having a mole ratio of glycine to sodium sulfate of about 1–5:1 and a pH of about 4.5–8.5 by: (a) cooling the starting solution to precipitate a first lot of glycine and form a first mother liquor; (b) separating the precipitated glycine from the first mother liquor; (c) recovering the separated glycine; (d) precipitating a first lot of sodium sulfate from the first mother liquor by evaporating water therefrom to form a first lot of precipitated sodium sulfate and a second mother liquor; (e) separating the precipitated sodium sulfate from the second mother liquor; (f) admixing the separated second mother liquor with water and a second lot of the aqueous starting solution to form a first resulting solution; (g) cooling the first resulting solution to form a second lot of precipitated glycine and a third mother liquor; (h) separating the second lot of precipitated glycine from the third mother liquor; (i) evaporating water from the third mother liquor to precipitate a second lot of precipitated sodium sulfate and form a fourth mother liquor; (j) separating the second lot of precipitated sodium sulfate from the fourth mother liquor; (k) admixing the separated fourth mother liquor with water and a third lot of the aqueous starting solution to form a second resulting solution; (1) cooling the second resulting solution to form a third crop of precipitated glycine and a fifth mother liquor; and (m) separating the third crop of precipitated glycine from the fifth mother liquor.

The separated fifth mother liquor can be concentrated to precipitate a third lot of sodium sulfate and to form a sixth mother liquor. Steps (j) through (m) can then be repeated. This procedure can be repeated indefinitely.

6 Claims, No Drawings

PROCESS FOR RECOVERING GLYCINE FROM SODIUM SULFATE SOLUTIONS

CROSS REFERENCE TO RELATED APPLICATIONS

This is a continuation-in-part of copending application Ser. No. 517,469, filed Oct. 24, 1974. Said application Ser. No. 517,469 is a continuation-in-part of application Ser. No. 442,543, filed Feb. 14, 1974, and now abandoned. Said application Ser. No. 442,543 is a continuation-in-part of application Ser. No. 319,539, filed Dec. 29, 1972, and now U.S. Pat. No. 3,808,269. The benefit of said earlier filed applications is claimed.

BACKGROUND OF THE INVENTION

This invention is in the field of glycine. More specifically, this invention is directed to a process for preparing pure or substantially pure glycine.

In the prior art glycine was prepared by; (a) hydrolyzing the nitrile ($NH_2CH_2CN$) with an aqueous alkaline earth metal hydroxide to form an alkaline earth metal salt of the amino acid (glycine); and (b) treating the alkaline earth metal salt with carbon dioxide to form the free amino acid (which remains in solution) and an alkaline earth metal carbonate (which precipitates). The amino acid (glycine) was then recovered. This method, as applied to the preparation of glycine, is taught by U.S. Pat. No. 2,388,189 (Schweitzer, 260/534).

It is desirable to replace the alkaline earth metal hydroxide of the prior art with sodium hydroxide because the latter has a lower equivalent weight than strontium and barium hydroxides, is more soluble than the alkaline earth metal hydroxides, is easier to handle under plant conditions and the ions of sodium, unlike those of barium, (a preferred alkaline earth metal hydroxide) are not toxic. However, such substitution introduces a complication in the separation and recovery of the amino acid (glycine) because sodium carbonate, unlike the alkaline earth metal carbonates, is readily soluble in water, thereby to render the separation and recovery of pure or substantially pure glycine difficult.

A method for separating certain free amino acids from a system comprising the amino acid, sodium chloride, and water is taught by U.S. Pat. No. 3,433,832 (Swanson et al., 260/534).

The Swanson et al. method is not applicable to an amino acid such as glycine which has a solubility greater than 35.0 parts per 100 parts of water at 100°C.

The process of our invention has been found to present an effective and convenient method for recovering glycine from a system consisting essentially of water, glycine and sodium sulfate. Such a system results where glycine is formed from glycinonitrile by hydrolyzing said nitrile with sodium hydroxide and treating the resulting sodium glycinate with sulfuric acid to convert the sodium salt (sodium glycinate) to the free amino acid (glycine). Our resulting aqueous glycine-sodium sulfate solution generally contains at least about 5% glycine, and, if it does not, water can be evaporated therefrom to adjust the glycine concentration thereof to at least about 5% (by weight).

The solid components (glycine or sodium sulfate, respectively) of the slurries formed in the process of our invention can be separated from the respective mother liquors by filtration, decantation, or centrifugation.

SUMMARY OF THE INVENTION

In summary, this invention is directed to a process for recovering glycine from an aqueous starting solution consisting essentially of water, glycine, and sodium sulfate, the aqueous starting solution having a temperature above about 35°C (e.g., between about 36°C and about its normal boiling point, or between about 40°C and 60°C, or between about 60°C and 95°C), a pH of 4.5–8.5, a mole ratio of glycine to sodium sulfate of 1–5:1, the process comprising (or consisting essentially of):

a. forming a first slurry consisting essentially of a first lot of precipitated solid glycine and a first mother liquor consisting essentially of water, dissolved glycine, and dissolved sodium sulfate by cooling the aqueous starting solution to a temperature above about 33°C (e.g., to about 34°C or 35°C, or a temperature above about 33°C and below about 60°C) effective for precipitation glycine;

b. separating the first mother liquor from the first lot of precipitated solid glycine (e.g., by centrifugation, decantation, or filtration) at a temperature above about 33°C (e.g., about 34°C or 35°C, or a temperature above about 33°C and below about 60°C) effective for separating the solid glycine, and recovering the separated solid glycine;

c. forming a second slurry consisting essentially of a first lot of precipitated solid sodium sulfate and a second mother liquor consisting essentially of water, dissolved glycine, and dissolved sodium sulfate by evaporating from the separated first mother liquor an amount of water effective for causing sodium sulfate to precipitate therefrom (from the evaporated first mother liquor) while maintaining the temperature of the resulting second slurry at a temperature effective for preventing the precipitation of solid glycine (e.g., within a temperature range between about 60°C and the normal boiling point of the second slurry (e.g., about 70°–100°C or 80°–95°C));

d. separating the second mother liquor from the first lot of precipitated solid sodium sulfate while maintaining the temperature of the second slurry at a temperature effective for preventing the precipitation of solid glycine (e.g., within a temperature range between about 60°C and the normal boiling point of the second slurry (e.g., 70°–100°C or 80°–95°C));

e. forming a first solution consisting essentially of: (i) water; (ii) dissolved glycine; and (iii) dissolved sodium sulfate by admixing the separated second mother liquor (which is preferably "hot," i.e., which preferably has a temperature effective for preventing the precipitation of solid glycine — i.e., a temperature between about 60°C and the normal boiling point of the second mother liquor) with water and a second lot of aqueous starting solution, the water being provided in an amount effective for preventing the precipitation of sodium sulfate where the first solution is cooled in a later recited cooling step;

f. forming a third slurry consisting essentially of a second lot of precipitated solid glycine and a third mother liquor consisting essentially of water, dissolved glycine, and dissolved sodium sulfate by cooling the first solution to a temperature above about 33°C effective for causing the second lot of solid glycine to precipitate therefrom (e.g., to a temperature within the range of about 34°–55°C, or 35°–40°C, or 36°–44°C, or to any temperature above about 33°C and below about 60°C);

g. separating the third mother liquor from the second lot of precipitated solid glycine (e.g., by centrifugation, decantation, or filtration) at a temperature above about 33°C (e.g., about 34°–55°C, or 35°–40°C, or 36°–44°C, or any temperature above about 33°C and below about 60°C) effective for separating the precipitated solid glycine, and recovering the separated solid glycine;

h. forming a fourth slurry consisting essentially of a second lot of precipitated solid sodium sulfate and a fourth mother liquor consisting essentially of water, dissolved glycine, and dissolved sodium sulfate by evaporating from the separated third mother liquor an amount of water effective for causing sodium sulfate to precipitate therefrom (from the evaporated resulting mixture) while maintaining the temperature of the resulting fourth slurry at a temperature effective for preventing the precipitation of solid glycine (e.g., within a temperature range between about 60°C and the normal boiling point of the second slurry (e.g., about 70°–100°C or 80°–95°C)); and i. separating the fourth mother liquor from the second lot of precipitated solid sodium sulfate while maintaining the temperature of the fourth slurry at a temperature effective for preventing the precipitation of solid glycine therefrom (e.g., within a temperature range between about 60°C and the normal boiling point of the second slurry (e.g., 70°–100°C or 80°–95°C)).

Steps (e), (f), (g), (h), and (i), supra, can be repeated indefinitely by admixing the separated mother liquor obtained in step (d) with water and starting solution as recited in step (e) and then proceeding as recited in steps (f) through (i), the water being provided in an amount effective for preventing the precipitation of sodium sulfate when the resulting admixture of mother liquor and water is cooled to precipitate glycine therefrom.

Where carrying on a long series of such runs (wherein steps (e) through (i) are repeated many times) it is generally preferred to remove a small portion of the separated mother liquor (e.g., about 1–10 percent or 3–6 percent or about 5 percent of such mother liquor) separated in step (i) to prevent the build up of color bodies and other undesired side-products which are present in small amounts in the starting aqueous solution. This removed portion is not admixed with starting aqueous solution in a repetition of step (e). It (the removed portion) can be discarded or processed separately to produce crude solid glycine which can be used as such or purified by conventional techniques such as recrystallization.

In steps (c) and/or (h) the evaporation can be conducted at temperatures (e.g., below about 55° or 60°C) at which glycine can be precipitated along with the sodium sulfate during the evaporation step providing steps (d) and/or (i), respectively, are conducted at temperatures above about 60°C so that any glycine which is precipitated in steps (c) or (h) is redissolved and is not separated from the mother liquor along with the precipitated solid sodium sulfate.

If the aqueous starting solution is too concentrated (so that sodium sulfate would precipitate on cooling) it (said starting solution) can be diluted (e.g., by adding water thereto) before starting step (a) of the Summary.

If the aqueous starting solution is too dilute (so that glycine will not precipitate on cooling) it (said starting solution) can be concentrated (by evaporating water therefrom) before starting step (a) of the Summary.

DESCRIPTION OF PREFERRED EMBODIMENTS

In preferred embodiments of the process of the above Summary:

1. The pH of the starting solution is 4.5–8.5 or 5.5–6.5. If the pH of the first aqueous mixture is not within the desired range (4.5–8.5 or 5.5–6.5), it can be brought to this range by adding caustic soda or the sodium salt of glycine to increase the pH, or sulfuric acid to lower the pH.
2. The mole ratio of glycine to sodium sulfate in the aqueous starting solution is 1:0.48–0.52.
3. The aqueous starting solution analyzes about 21–26% glycine.
4. The aqueous starting solution is formed by:
   a. saponifying glycinonitrile with sodium hydroxide in an aqueous system to form $NH_2CH_2COONa$; and
   b. acidifying the $H_2NCH_2COONa$ with sulfuric acid in an aqueous system to form glycine and sodium sulfate.

DETAILED DESCRIPTION OF THE INVENTION

Because of our disclosure it will be readily apparent to those skilled in the art that water can be evaporated from the separated first and third mother liquors of the above Summary and the above preferred embodiments at a reduced pressure (i.e., a pressure under 760 mm of mercury absolute) at normal atmospheric pressure, or at an elevated pressure (i.e., a pressure greater than 760 mm of mercury absolute). However, no particular advantage is gained by using reduced or elevated pressures and we generally prefer to operate at atmospheric pressure.

We generally prefer to precipitate (and separate) glycine from our glycine containing solutions at a temperature above about 30°C (generally above about 32°C, or 33°C, or 34°C) to prevent precipitation of sodium sulfate. Because of our disclosure, one skilled in the art can readily determine operating temperatures for systems comprising or consisting essentially of glycine, sodium sulfate, and water.

We prefer to prepare our glycine from the corresponding nitrile according to the following sequence of reactions:

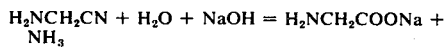
$H_2NCH_2CN + H_2O + NaOH = H_2NCH_2COONa + NH_3$

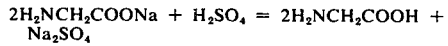
$2H_2NCH_2COONa + H_2SO_4 = 2H_2NCH_2COOH + Na_2SO_4$

Where an excess of sodium hydroxide is added in the saponification step sufficient sulfuric acid can be added in the acidification step to neutralize such excess (free) sodium hydroxide according to the following equation:

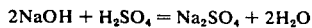
$2NaOH + H_2SO_4 = Na_2SO_4 + 2H_2O$

The pH can be adjusted during (or after) the acidification step to a level (pH 4.5–8.5 or 5.5–6.5, or 6) preferred for separating the amino acid.

If too much sulfuric acid is added during the acidification step or where adjusting the pH, the pH can be increased by neutralizing the excess acid with sodium hydroxide or with the sodium salt of the amino acid.

If highly pure amino acid (glycine) is desired the recovered (product) amino acid can be dissolved in hot water and recrystallized therefrom by cooling to form a solid phase consisting essentially of the recrystallized amino acid and a liquid phase consisting essentially of a solution of the amino acid in water. The solid phase (amino acid) can be separated from the liquid phase and recovered. At least a portion (e.g., up to about 80–99 percent, or 90–98 percent, or 100 percent) of the liquid phase from which the solid phase was separated can be admixed with the water used to dissolve the amino acid in a subsequent recrystallization. Alternatively, the liquid phase separated from the solid amino acid in this purification step can be admixed with the aqueous starting solution described in the above Summary or with the second mother liquor or the fourth mother liquor described in said Summary.

In the process of our invention centrifugation, decantation, or filtration can be used to separate aqueous mother liquor from a precipitate (precipitated glycine or precipitated sodium sulfate).

Glycine separated by the process of this invention can, if desired, be washed. For example, it can be washed with cool or cold water (e.g., water having the temperature of about 5°–25°C up to about 30°C) or, alternatively with a solution of glycine (e.g., a saturated or nearly saturated aqueous solution of glycine). The solubility of glycine in water is 20.0% at 25°C, 23.0% at 35°C, and 36.1% at 80°C.

The temperature at which glycine is precipitated and separated from a mother liquor depends upon the concentration of the glycine in the solution from which it (glycine) is precipitated. For example, higher temperatures can be used with systems containing 15–20 percent or more glycine than can be used with systems containing 5–10 percent or less glycine.

Because of our disclosure it will be readily understood by those skilled in the art that aqueous starting solutions containing considerably more than 5% amino acid are preferred for use in the process of our invention because less water will have to be evaporated to cause the sodium sulfate to precipitate where using such aqueous starting solutions than where using starting solutions containing about 20% or more amino acid.

Obviously, starting solutions containing 1% or less amino acid can be used, but large amounts of water must be evaporated where using such solutions.

Because of our disclosure it will also be readily apparent to those skilled in the art that water can be evaporated from systems (such as the first mother liquor of the above Summary or the resulting mixture of said Summary) to precipitate sodium sulfate therefrom at a temperature at which glycine will precipitate along with sodium sulfate providing the thus formed slurry is heated to a temperature (e.g., about 60°C to the normal boiling point of such slurry or to any temperature between about 60°C and such boiling point) effective for dissolving the precipitated glycine before separating the precipitated sodium sulfate from the mother liquor from which it (the sodium sulfate) precipitated.

The instant invention will be better understood by referring to the following specific but nonlimiting procedures. It is understood that said invention is not limited by these procedures which are offered merely as illustrations; it is also understood that modification can be made without departing from the spirit and scope of the invention.

PROCEDURE 1

(Preparation of Aqueous Glycine-Sodium Sulfate Solution)

An aqueous ammoniacal solution of glycinonitrile containing 2804 g (50 moles) of glycinonitrile is fed into an aqueous sodium hydroxide solution (20% sodium hydroxide) containing 2,040 g (51 moles) of sodium hydroxide at 50°–60°C. The resulting mixture is then boiled until free of ammonia. The resulting ammonia free sodium glycinate solution is cooled to 80°C, bleached with hydrogen peroxide (5 ml of 36% $H_2O_2$), treated with charcoal and filtered to remove color bodies, cooled to room temperature (ca. 25°C), and diluted to 12.13 Kg with water. The resulting aqueous solution consists essentially of 40% sodium glycinate and 0.3% sodium hydroxide. Said solution is substantially free of disodium iminodiacetate and it contains only trace quantities of color bodies and other undesired side products. A starting aqueous solution having a pH of 6 and consisting essentially of water, sodium sulfate and glycine is formed by adding 93% sulfuric acid (2,662 g) to the aforesaid 12.13 Kg of sodium glycinate solution. Said starting aqueous solution is designated "Starting Solution 1."

PROCEDURE 2

(Recovery of Glycine — First Cycle)

A quantity of Starting Solution 1 weighing 1,183 g and containing 4 moles (300 g) is diluted with 133 g of water and the resulting diluted starting solution is cooled to 35°C to form a first slurry consisting essentially of a first crop of precipitated glycine and a first mother liquor.

The first crop of glycine is separated from the first mother liquor by centrifuging at 35°C and the separated first crop of glycine is recovered, dried, and weighed (66 g).

The separated first mother liquor is boiled to evaporate 303 g of water therefrom to form a second slurry consisting essentially of a first crop of precipitated sodium sulfate and a second mother liquor.

The second slurry is cooled to 80°C and centrifuged at 80°C to separate the first crop of sodium sulfate from the second mother liquor. The separated first crop of sodium sulfate is recovered, dried and weighed (111 g).

PROCEDURE 3

(Recovery of Glycine — Second Cycle)

All of the separated second mother liquor (from Procedure 2, Cycle 1) is admixed with 159 g of water and an 1,183 g portion of Starting Solution 1 to form a first resulting solution which is cooled to 35°C to form a third slurry consisting essentially of a second crop of precipitated glycine and a third mother liquor.

The third slurry is centrifuged at 35°C to separate the second crop of precipitated glycine from the third mother liquor. The separated second crop of precipitated glycine is recovered, dried and weighed (154 g).

The separated third mother liquor is boiled to evaporate 477 g of water therefrom and to form a fourth slurry consisting essentially of a second crop of precipitated sodium sulfate and a fourth mother liquor.

The fourth slurry is cooled to 80°C and centrifuged at 80°C to separate the second crop of precipitated sodium sulfate from the fourth mother liquor. The separated second crop of sodium sulfate is dried and weighed (188 g).

PROCEDURE 4

(Recovery of Glycine — Third Cycle)

All of the separated fourth mother liquor (from Procedure 3, Cycle 2) is admixed with 179 g of water and an 1,183 g portion of Starting Solution 1 to form a second resulting solution which is cooled to 35°C to form a fifth slurry consisting essentially of a third crop of glycine and a fifth mother liquor The fifth slurry is centrifuged at 35°C to separate the third crop of precipitated glycine from the fifth mother liquor. The separated third crop of precipitated glycine is recovered, dried and weighed (217 g).

The separated fifth mother liquor is boiled to evaporate 605 g of water therefrom and to form a sixth slurry consisting essentially of a third crop of precipitated sodium sulfate and a sixth mother liquor.

The sixth slurry is cooled to 80°C and centrifuged at 80°C to separate the third crop of precipitated sodium sulfate from the sixth mother liquor. The separated third crop of sodium sulfate is dried and weighed (229 g).

PROCEDURE 5

(Recovery of Glycine - Fourth Cycle)

All of the separated sixth mother liquor (from Procedure 4, Cycle 3) is admixed with 146 g of water and an 1,183 g portion of Starting Solution 1 to form a third resulting solution which is cooled to 35°C to form a seventh slurry consisting essentially of a fourth crop of glycine and a seventh mother liquor.

The seventh slurry is centrifuged at 35°C to separate the fourth crop of precipitated glycine from the seventh mother liquor. The separated fourth crop of precipitated glycine is recovered, dried and weighed (255 g).

The separated seventh mother liquor is boiled to evaporate 643 g of water therefrom and to form an eighth slurry consisting essentially of a fourth crop of precipitated sodium sulfate and an eighth mother liquor.

The eighth slurry is cooled to 80°C and centrifuged at 80°C to separate the fourth crop of precipitated sodium sulfate from the eighth mother liquor. The separated fourth crop of sodium sulfate is dried and weighed (251 g).

PROCEDURE 6

(Recovery of Glycine — Fifth Cycle)

All of the separated eighth mother liquor (from Procedure 5, Cycle 4) is admixed with 163 g of water and an 1,183 g portion of Starting Solution 1 to form a fourth resulting solution which is cooled to 35°C to form a ninth slurry consisting essentially of a fifth crop of glycine and a ninth mother liquor.

The ninth slurry is centrifuged at 35°C to separate the fifth crop of precipitated glycine from the ninth mother liquor. The separated fifth crop of precipitated glycine is recovered, dried and weighed (270 g).

The separated ninth mother liquor is boiled to evaporate 681 g of water therefrom and to form a tenth slurry consisting essentially of a fifth crop of precipitated sodium sulfate and a tenth mother liquor.

The tenth slurry is cooled to 80°C and centrifuged at 80°C to separate the fifth crop of precipitated sodium sulfate from the tenth mother liquor. The separated fifth crop of sodium sulfate is dried and weighed (266 g).

PROCEDURE 7

(Recovery of Glycine — Sixth Cycle)

All of the separated tenth mother liquor (from Procedure 6, Cycle 5) is admixed with 173 g of water and an 1,183 g portion of Starting Solution 1 to form a fifth resulting solution which is cooled to 35°C to form an eleventh slurry consisting essentially of a sixth crop of glycine and an eleventh mother liquor.

The eleventh slurry is centrifuged at 35°C to separate the sixth crop of precipitated glycine from the eleventh mother liquor. The separated sixth crop of precipitated glycine is recovered, dried and weighed (280 g).

The separated eleventh mother liquor is boiled to evaporate 706 g of water therefrom and to form a twelth slurry consisting essentially of a sixth crop of precipitated sodium sulfate and a twelth mother liquor.

The twelth slurry is cooled to 80°C and centrifuged at 80°C to separate the sixth crop of precipitated sodium sulfate from the twelth mother liquor. The separated sixth crop of sodium sulfate is dried and weighed (276 g).

The separated twelth mother liquor weighed 1,962 g.

PROCEDURE 8

(Recovery of Glycine — Seventh Cycle)

A 1,864 g portion of the separated twelfth mother liquor (from Procedure 7, Cycle 6) is admixed with 170 g of water and an 1,183 g portion of Starting Solution 1 to form a sixth resulting solution which is cooled to 35°C to form a thirteenth slurry consisting essentially of a seventh crop of glycine and a thirteenth mother liquor.

The thirteenth slurry is centrifuged at 35°C to separate the seventh crop of precipitated glycine from the thirteenth mother liquor. The separated seventh crop of precipitated glycine is recovered, dried and weighed (278 g).

The separated thirteenth mother liquor is boiled to evaporate 702 g of water therefrom and to form a fourteenth slurry consisting essentially of a seventh crop of precipitated sodium sulfate and a fourteenth mother liquor.

The fourteenth slurry is cooled to 80°C and centrifuged at 80°C to separate the seventh crop of precipitated sodium sulfate from the fourteenth mother liquor. The separated seventh crop of sodium sulfate is dried and weighed (273 g).

The separated fourteenth mother liquor weighed 1,941 g.

PROCEDURE 9

(Recovery of Glycine - Eighth Cycle)

A 1,843 g portion of the separated fourteenth mother liquor (from Procedure 8, Cycle 7) is admixed with 160 g of water and an 1,183 g portion of Starting Solution 1 to form a seventh resulting solution which is cooled to 35°C to form a fifteenth slurry consisting essentially of an eighth crop of glycine and a fifteenth mother liquor.

The fifteenth slurry is centrifuged at 35°C to separate the eighth crop of precipitated glycine from the fifteenth mother liquor. The separated eighth crop of precipitated glycine is recovered, dried and weighed (276 g).

The separated fifteenth mother liquor is boiled to evaporate 697 g of water therefrom and to form a sixteenth slurry consisting essentially of an eighth crop of precipitated sodium sulfate and a sixteenth mother liquor.

The sixteenth slurry is cooled to 80°C and centrifuged at 80°C to separate the eighth crop of precipitated sodium sulfate from the sixteenth mother liquor. The separated eighth crop of sodium sulfate is dried and weighed (271 g).

The separated sixteenth mother liquor weighed 1,928 g.

PROCEDURE 10

(Recovery of Glycine — Ninth Cycle)

A 1,832 g portion of the separated sixteenth mother liquor (from Procedure 9, Cycle 8) is admixed with 167 g of water and an 1,183 g portion of Starting Solution 1 to form an eighth resulting solution which is cooled to 35°C to form a seventeenth slurry consisting essentially of a ninth crop of glycine and a seventeenth mother liquor.

The seventeenth slurry is centrifuged at 35°C to separate the ninth crop of precipitated glycine from the seventeenth mother liquor. The separated ninth crop of precipitated glycine is recovered, dried and weighed (275 g).

The separated seventeenth mother liquor is boiled to evaporate 693 g of water therefrom and to form an eighteenth slurry consisting essentially of a ninth crop of precipitated sodium sulfate and an eighteenth mother liquor.

The eighteenth slurry is cooled to 80°C and centrifuged at 80°C to separate the ninth crop of precipitated sodium sulfate from the eighteenth mother liquor. The separated ninth crop of sodium sulfate is dried and weighed (270 g).

The separated eighteenth mother liquor weighed 1,921 g.

PROCEDURE 11

(Recovery of Glycine — Tenth Cycle)

A 1,826 g portion of the separated eighteenth mother liquor (from Procedure 10, Cycle 9) is admixed with 165 g of water and an 1,183 g portion of Starting Solution 1 to form a ninth resulting solution which is cooled to 35°C to form a nineteenth slurry consisting of a tenth crop of glycine and a nineteenth mother liquor.

The nineteenth slurry is centrifuged at 35°C to separate the tenth crop of precipitated glycine from the nineteenth mother liquor. The separated tenth crop of precipitated glycine is recovered, dried and weighed (274 g).

The separated nineteenth mother liquor is boiled to evaporate 725 g of water therefrom and to form a twentieth slurry consisting essentially of a tenth crop of precipitated sodium sulfate and a twentieth mother liquor. The twentieth slurry is cooled to 80°C and centrifuged at 80°C to separate the tenth crop of precipitated sodium sulfate from the twentieth mother liquor. The separated tenth crop of sodium sulfate is dried and weighed (264 g).

The separated twentieth mother liquor weighs 1,878 g.

PROCEDURE 12

(Recovery of Glycine — Eleventh Cycle)

All of the separated twentieth mother liquor (from Procedure 11, Cycle 10) is cooled to 35°C to form a twenty-first slurry consisting essentially of a twenty-first mother liquor and an eleventh crop of precipitated glycine.

The twenty-first slurry is centrifuged at 35°C to separate the eleventh crop of precipitated glycine from the twenty-first mother liquor. The separated eleventh crop of precipitated glycine is recovered, dried and weighed (228 g).

The separated twenty-first mother liquor (which contains 306 g of glycine and 392 g of sodium sulfate) is not processed further. However, if desired, it (the separated twenty-first mother liquor) can be further processed in the eleventh and succeeding cycles.

In Cycles 1-11 (Procedures 2-12) a total of 3,000 g of glycine and a total of 2,870 g of sodium sulfate were charged. A total of 2,573 g of glycine and 2,399 g of sodium sulfate are recovered corresponding to a glycine recovery of 85.8% and a sodium sulfate recovery of 83.6%.

These values (recoveries) are exclusive of 110 g glycine and 79 g of sodium sulfate discarded at the start of Cycles 7, 8, 9, and 10. Said recoveries are also exclusive of 306 g of glycine and 392 g of sodium sulfate remaining in the separated twenty-first mother liquor at the end of Cycle 11. Calculations which include these nonrecovered quantities of glycine (416 g) and sodium sulfate (471 g) show that 99.6% of the glycine charged and 100% of the sodium sulfate charged are accounted for.

Glycine is an article of commerce. It is useful as an additive in metal plating baths, as a nutrient supplement for animal feeds and fermentation broths, and as a flavor enhancing agent in food.

As herein the term "percent (%)" means parts per hundred and parts means parts by weight unless otherwise defined where used.

As used herein the term "mole" has its generally accepted meaning. A mole of a substance is that quantity which contains the same number of molecules of the substance as there are atoms in 12 grams of pure $^{12}C$.

As used herein the term "g" means gram or grams and the term "Kg" means kilogram or kilograms. A kilogram is 1000 grams.

We claim:

1. A process for recovering glycine from an aqueous starting solution consisting essentially of water, glycine, and sodium sulfate, the aqueous starting solution having a temperature above about 35°C, a pH of 4.5-8.5, a mole ratio of glycine to sodium sulfate of 1-5:1, the process comprising:

a. forming a first slurry consisting essentially of a first lot of precipitated solid glycine and a first mother liquor consisting essentially of water, dissolved glycine, and dissolved sodium sulfate by cooling the aqueous starting solution to a temperature above about 33°C effective for precipitating glycine;

b. separating the first mother liquor from the first lot of precipitated solid glycine while maintaining the first slurry at a temperature above about 33°C effective for separating the solid glycine, and recovering the separated solid glycine;

c. forming a second slurry consisting essentially of a first lot of precipitated solid sodium sulfate and a second mother liquor consisting essentially of water, dissolved glycine, and dissolved sodium sulfate by evaporating from the separated first mother liquor an amount of water effective for causing sodium sulfate to precipitate while maintaining the temperature of the resulting second slurry at a temperature effective for preventing the precipitation of solid glycine;

d. separating the second mother liquor from the first lot of precipitated solid sodium sulfate while maintaining the temperature of the second slurry at a temperature effective for preventing the precipitation of solid glycine;

e. forming a first solution consisting essentially of: (i) water; (ii) dissolved glycine; and (iii) dissolved sodium sulfate by admixing the separated second mother liquor with water and a second lot of aqueous starting solution, the water being provided in an amount effective for preventing the precipitation of sodium sulfate where the first solution is cooled in a later recited cooling step;

f. forming a third slurry consisting essentially of a second lot of precipitated solid glycine and a third mother liquor consisting essentially of water, dissolved glycine, and dissolved sodium sulfate by cooling the first solution to a temperature above about 33°C effective for causing the second lot of solid glycine to precipitate;

g. separating the third mother liquor from the second lot of precipitated solid glycine while maintaining the third slurry at a temperature above 33°C effective for separating the solid glycine, and recovering the separated solid glycine;

h. forming a fourth slurry consisting essentially of a second lot of precipitated solid sodium sulfate and a fourth mother liquor consisting essentially of water, dissolved glycine, and dissolved sodium sulfate by evaporating from the separated third mother liquor an amount of water effective for causing sodium sulfate to precipitate while maintaining the temperature of the resulting fourth slurry at a temperature effective for preventing the precipitation of solid glycine; and i. separating the fourth mother liquor from the second lot of precipitated solid sodium sulfate while maintaining the temperature of the fourth slurry at a temperature effective for preventing the precipitation of solid glycine.

2. The process of claim 1 in which the pH of the aqueous starting solution is 5.5–6.5.

3. The process of claim 1 in which the mole ratio of glycine to sodium sulfate is 1:0.48–0.52.

4. The process of claim 1 in which the aqueous starting solution analyzes about 21–26% glycine.

5. The process of claim 1 in which the aqueous starting solution is prepared by:
 a. saponifying glycinonitrile with sodium hydroxide in an aqueous system to form $NH_2CH_2COONa$; and
 b. acidifying the $H_2NCH_2COONa$ with sulfuric acid in an aqueous system to form glycine and sodium sulfate.

6. A process for recovering glycine from an aqueous starting solution consisting essentially of water, glycine, and sodium sulfate, the aqueous starting solution having a temperature above about 35°C, a pH of 4.5–8.5, a mole ratio of glycine to sodium sulfate of 1–5:1, the process comprising:

a. forming a first slurry consisting essentially of a first lot of precipitated solid glycine and a first mother liquor consisting essentially of water, dissolved glycine, and dissolved sodium sulfate by cooling the aqueous starting solution to a temperature above about 33°C effective for precipitating glycine;

b. separating the first mother liquor from the first lot of precipitated solid glycine while maintaining the first slurry at a temperature above about 33°C effective for separating the solid glycine, and recovering the separated solid glycine;

c. forming a second slurry consisting essentially of a first lot of precipitated solid sodium sulfate and a second mother liquor consisting essentially of water, dissolved glycine, and dissolved sodium sulfate by evaporating from the separated first mother liquor an amount of water effective for causing sodium sulfate to precipitate while maintaining the temperature of the resulting second slurry at a temperature effective for preventing the precipitation of solid glycine;

d. separating the second mother liquor from the first lot of precipitated solid sodium sulfate while maintaining the temperature of the second slurry at a temperature effective for preventing the precipitation of solid glycine;

e. forming a first solution consisting essentially of: (i) water; (ii) dissolved glycine; and (iii) dissolved sodium sulfate by admixing the separated second mother liquor with water and a second lot of aqueous starting solution, the water being provided in an amount effective for preventing the precipitation of sodium sulfate where the first solution is cooled in a later recited cooling step; and f. forming a third slurry consisting essentially of a second lot of precipitated solid glycine and a third mother liquor consisting essentially of water, dissolved glycine, and dissolved sodium sulfate by cooling the first solution to a temperature above about 33°C effective for causing the second lot of solid glycine to precipitate.

* * * * *